US00PP36928P2

(12) United States Plant Patent
van Dijk

(10) Patent No.: US PP36,928 P2
(45) Date of Patent: Sep. 2, 2025

(54) ***ANTHURIUM* PLANT NAMED 'AN2741745'**

(50) Latin Name: *Anthurium andreanum*
Varietal Denomination: AN2741745

(71) Applicant: ANTHURA B.V., Bleiswijk (NL)

(72) Inventor: Jan van Dijk, Bleiswijk (NL)

(73) Assignee: ANTHURA B.V., Bleiswijk (NL)

( * ) Notice: Subject to any disclaimer, the term of this patent is extended or adjusted under 35 U.S.C. 154(b) by 0 days.

(21) Appl. No.: 18/817,118

(22) Filed: Aug. 27, 2024

(51) Int. Cl.
*A01H 5/02* (2018.01)
*A01H 6/10* (2018.01)

(52) U.S. Cl.
USPC ..... Plt./368

(58) Field of Classification Search
USPC ..... Plt./365, 368
See application file for complete search history.

*Primary Examiner* — Susan McCormick Ewoldt
(74) *Attorney, Agent, or Firm* — C. Anne Whealy

(57) ABSTRACT

A new and distinct cultivar of *Anthurium* plant named 'AN2741745', characterized by its upright to outwardly arching and uniform plant habit; freely clumping growth habit; bushy and dense plants; narrowly cordate dark green-colored leaves; freely flowering habit; inflorescences that are positioned within to slightly above the foliar plane on strong and mostly upright scapes; broadly cordate purplish red-colored spathes with light purple-colored venation and spadices that are pink and yellow in color; and durable spathes that impart good inflorescence longevity.

2 Drawing Sheets

Figure 1:
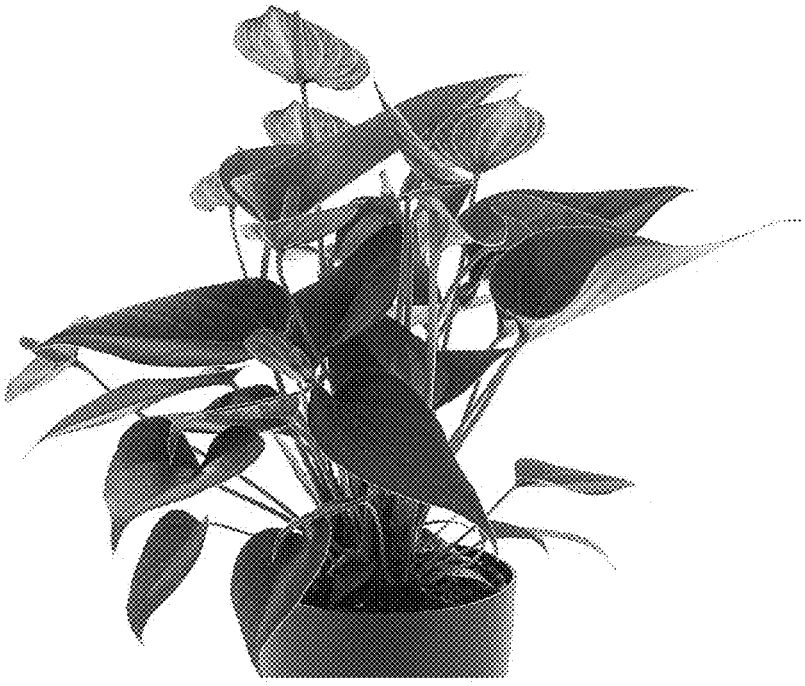

Botanical designation: *Anthurium andreanum.*
Cultivar denomination: 'AN2741745'.

BACKGROUND OF THE INVENTION

The present invention relates to a new and distinct cultivar of *Anthurium* plant, botanically known as *Anthurium andreanum* and hereinafter referred to by the name 'AN2741745'.

The new *Anthurium* plant is a product of a controlled breeding program conducted by the Inventor in Bleiswijk, The Netherlands. The objective of the breeding program is to create new medium-sized and freely-clumping *Anthurium* plants with attractive and durable spathes.

The new *Anthurium* plant originated from a cross-pollination made by the Inventor in April 2012 in Bleiswijk, The Netherlands of a proprietary selection of *Anthurium andreanum* identified as code number 09-023506-0001, not patented, as the female, or seed, parent with a proprietary selection of *Anthurium andreanum* identified as code number 09-022667-0003, not patented, as the male, or pollen, parent. The new *Anthurium* was discovered and selected by the Inventor as a single flowering plant within the progeny of the stated cross-pollination in a controlled greenhouse environment in Bleiswijk, The Netherlands in July 2014.

Asexual reproduction of the new *Anthurium* plant by in vitro meristem propagation in a controlled environment in Bleiswijk, The Netherlands since November 2015 has shown that the unique features of this new *Anthurium* are stable and reproduced true to type in successive generations of asexual reproduction.

SUMMARY OF THE INVENTION

Plants of the new *Anthurium* have not been observed under all possible combinations of environmental conditions and cultural practices. The phenotype may vary somewhat with variations in environment conditions such as temperature and light intensity, without, however, any variance in genotype.

The following traits have been repeatedly observed and are determined to be the unique characteristics of 'AN2741745'. These characteristics in combination distinguish 'AN2741745' as a new and distinct *Anthurium* plant:

1. Upright to outwardly arching and uniform plant habit.
2. Freely clumping growth habit; bushy and dense plants.
3. Narrowly cordate dark green-colored leaves.
4. Freely flowering habit.
5. Inflorescences that are positioned within to slightly above the foliar plane on strong and mostly upright scapes.
6. Broadly cordate purplish red-colored spathes with light purple-colored venation and spadices that are pink and yellow in color.
7. Durable spathes that impart good inflorescence longevity.

Plants of the new *Anthurium* differ primarily from plants of the female parent selection in the following characteristics:

1. Spathes of plants of the new *Anthurium* are purplish red in color whereas spathes of plants of the female parent selection are pink in color.
2. Spathes of plants of the new *Anthurium* are slightly concave whereas spathes of plants of the female parent selection are flat to slightly convex.
3. Spadices of plants of the new *Anthurium* are longer than spadices of plants of the female parent selection.

Plants of the new *Anthurium* differ primarily from plants of the male parent selection in spadix color as spadices of plants of the new *Anthurium* are pink and yellow in color whereas spadices of plants of the male parent selection are white and green in color.

Plants of the new *Anthurium* can also be compared to plants of *Anthurium andreanum* 'AN2667176', disclosed in U.S. Plant Pat. No. 35,341. In side-by-side comparisons, plants of the new *Anthurium* differ primarily from plants of 'AN2667176' in the following characteristics:

1. Plants of the new *Anthurium* are not as freely clumping as plants of 'AN2667176'.
2. Spathes of plants of the new *Anthurium* are purplish red in color whereas spathes of plants of 'AN2667176' are red in color.
3. Plants of the new *Anthurium* have longer spadices than plants of 'AN2667176'.

BRIEF DESCRIPTION OF THE PHOTOGRAPHS

The accompanying photographs illustrate the overall appearance of the new *Anthurium*. The photographs show the colors as true as it is reasonably possible to obtain in colored reproductions of this type. Colors in the photographs may differ slightly from the color values cited in the detailed botanical description which accurately describe the colors of the new *Anthurium*.

The photograph on the first sheet (FIG. 1) is a side perspective view of a typical plant of 'AN2741745' grown in a container.

Figure 2:
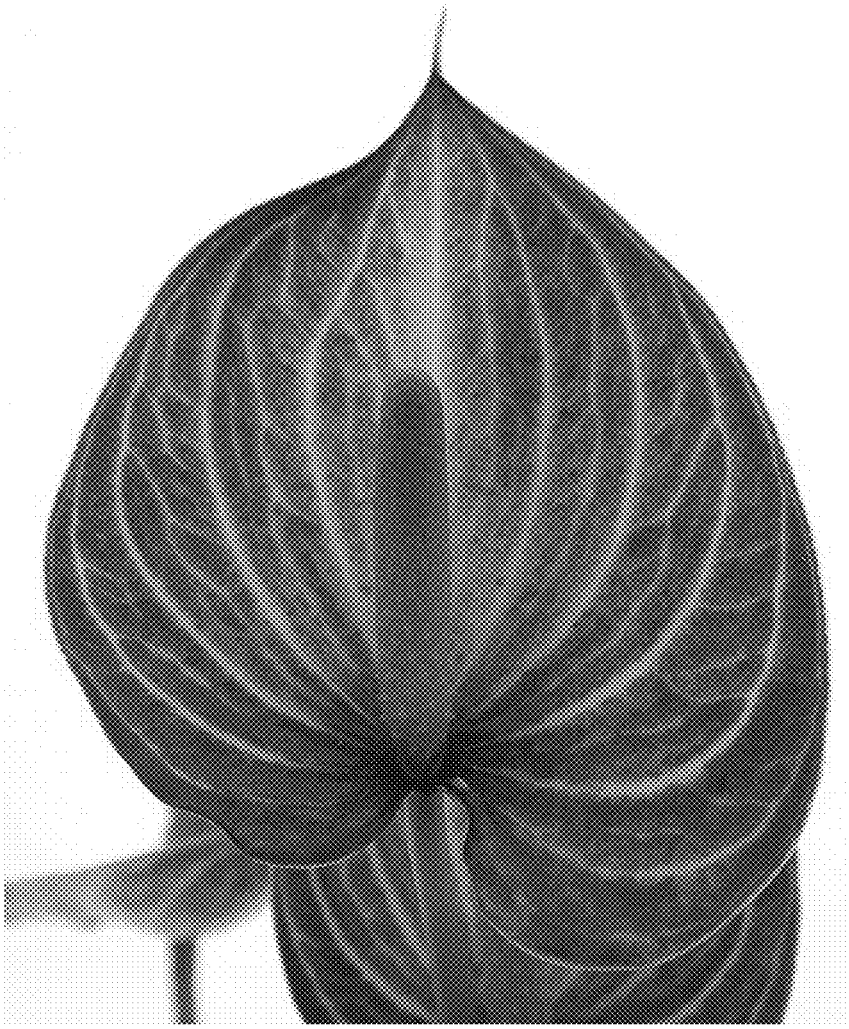

The photograph on the second sheet (FIG. 2) is a close-up view of a typical inflorescence of 'AN2741745'.

DETAILED BOTANICAL DESCRIPTION

The aforementioned photographs and following observations and measurements describe plants grown in 12-cm containers during the summer in a glass-covered greenhouse in Bleiswijk, The Netherlands. Plants were grown under conditions and practices which approximate those generally used in commercial *Anthurium* production. During the production of the plants, day and night temperatures ranged from about 19° C. to 22.5° C. and light levels ranged from 100 μmol to 200 μmol. Plants were ten months old when the photographs and the detailed description were taken. In the following description, color references are made to The Royal Horticultural Society Colour Chart, 2015 Edition, except where general terms of ordinary dictionary significance are used.

Botanical classification: *Anthurium andreanum* 'AN2741745'.

Parentage:

*Female, or seed, parent*.—Proprietary selection of *Anthurium andreanum* identified as code number 09-023506-0001, not patented.

*Male, or pollen, parent*.—Proprietary selection of *Anthurium andreanum* identified as code number 09-022667-0003, not patented.

Propagation:

*Type*.—By in vitro meristem propagation.

*Time to initiate roots, summer and winter*.—About two weeks at temperatures about 19° C. to 22.5° C.

*Time to produce a rooted young plant, summer and winter*.—About six to eight weeks at temperatures about 19° C. to 22.5° C.

*Root description*.—Medium in thickness, fibrous; typically creamy white slightly tinged with yellowish pink in color, actual color of the roots is dependent on substrate composition, water quality, fertilizer type and formulation, substrate temperature and physiological age of roots.

*Rooting habit*.—Freely branching, medium density.

Plant description:

*Plant shape*.—Upright to outwardly spreading and uniform plant habit; overall shape, spherical to flatted spherical or flattened rhomboidal.

*Growth habit*.—Freely clumping habit with about four clumps developing per plant imparting a bushy and dense appearance; moderately vigorous growth habit and moderate growth rate.

*Plant height, from soil level to top of leaf plane*.—About 25.9 cm.

*Plant height, from soil level to top of inflorescences*.—About 30 cm.

*Plant diameter or spread*.—About 40.5 cm.

Leaf description:

*Arrangement*.—Alternate; simple; about four leaves per clump.

*Length*.—About 15.9 cm.

*Width*.—About 8.2 cm.

*Shape*.—Narrowly cordate to cordate/lanceolate.

*Apex*.—Narrowly apiculate with a short mucronate tip.

*Base*.—Cordate; basal lobes free.

*Margin*.—Entire; slightly and coarsely undulate.

*Texture and luster, upper and lower surfaces*.—Smooth, glabrous; moderately to strongly coriaceous; glossy.

*Venation pattern*.—Pinnate.

*Color*.—Developing leaves, upper surface: Close to a blend of NN137A and 146A. Developing leaves, lower surface: Close to 146B. Fully expanded leaves, upper surface: Close to a blend of NN137A and 139A; venation, close to 143B. Fully expanded leaves, lower surface: Close to 146B; venation, close to 144B.

*Petioles*.—Length: About 14.5 cm. Diameter: Distally, about 3 mm; proximally, about 4 mm. Strength: Strong. Texture and luster, upper and lower surfaces: Smooth, glabrous; slightly glossy. Color, upper surface: Close to a blend of 143A and 143B. Color, lower surface: Close to 144A. Geniculum length: About 2.1 cm. Geniculum diameter: About 3.5 mm by 4 mm. Geniculum texture, upper and lower surfaces: Smooth, glabrous. Geniculum color, upper surface: Close to 144A. Geniculum color, lower surface: Close to 144B. Wing length: About 1.4 cm. Wing diameter: About 4 mm. Wing color: Close to 143A; towards the margins, close to 144A.

Inflorescence description:

*Inflorescence arrangement and flowering habit*.—Spathes with spadices held within and slightly above the foliar plane on strong and erect scapes; flowering structures arise from leaf axils; freely and continuous flowering year-round in controlled temperature greenhouses in The Netherlands; typically about nine developing and developed inflorescences per plant at one time; inflorescence development commences about 2.5 to 3.5 months after planting.

*Inflorescence longevity*.—Depending on temperature, spathes maintain good substance for about two months on the plant; inflorescences persistent.

*Fragrance*.—None detected.

*Spathes*.—Length: About 8.1 cm. Width: About 6.2 cm. Shape: Broadly cordate; slightly concave. Apex: Broadly apiculate with a mucronate apex. Base: Cordate. Margin: Entire; not undulate to slightly and coarsely undulate. Aspect: About 50° from the scape axis. Texture and luster, upper and lower surfaces: Smooth, glabrous; coriaceous; somewhat glossy. Color: When developing, front surface: Close to 64B to 64D; towards the margins, and base, close to 71A and a blend of 71A and N186D; at the apex, close to 144B; venation, close to 75D and 186D. When developing, rear surface: Close to 63B and 186B; at the margins, close to 71A; at the apex, close to 144B; venation, close to 155C. Fully developed, front surface: Close to 59C; towards the margins, and base, close to 59B, 60A and 60B; at the apex, close to 145A and 145B; venation, close to 75D and 76D; with subsequent development, colors becoming closer to 179B and 179C, at the centers, tinged with close to 160B; towards the margins, apex and base, close to 180A and 180B, and at the apex, close to 151D with venation, close to 144D. Fully developed, rear surface: Close to 59C and 59D; towards the margins, close to 61A; towards the apex, close to 75D and at the apex, close to 144B with venation, close to 75D; with subsequent development, colors becoming closer to 181C and 181D and towards the margins, apex and base, close to 181A and 181B, at the apex, close to 151D with venation, close to 144B.

*Spadices*.—Length: About 3.7 cm. Diameter: About 7 mm. Shape: Columnar, slightly tapering towards the apex; apex, obtuse; base, obtuse; in cross-section, rounded. Aspect: About 45° from the spathe axis and about 2.5° from the scape axis. Color: Immature: Close to 161B; towards the apex, close to 150A. Mature: Close to 182D; towards the apex, close to 14C. Flowers: Type: Hermaphroditic. Quantity per spadix: Numerous, about 250. Height: About 0.8 mm. Diameter: About 2.5 mm. Shape: Roughly square. Anther color: Close to 182D. Pollen amount: Moderate. Pollen color: Close to 158D. Stigma color: Close to 156D.

*Scapes*.—Length: About 20.1 cm. Diameter: About 4 mm. Strength: Strong. Aspect: About 20° from vertical. Color: Close to 144A; distally, tinged with close to 43A.

*Seed and fruit*.—To date, seed and fruit development has not been observed on plants of the new *Anthurium*.

Pathogen & pest resistance: To date, plants of the new *Anthurium* have not been observed to be resistant to pathogens or pests common to *Anthurium* plants.

Temperature tolerance: Plants of the new *Anthurium* have been observed to be tolerant to high temperatures about 30° C. and to be hardy to USDA Hardiness Zone 10.

It is claimed:

1. A new and distinct *Anthurium* plant named 'AN2741745' as herein illustrated and described.

* * * * *